(12) United States Patent
Cakic et al.

(10) Patent No.: US 12,048,443 B2
(45) Date of Patent: Jul. 30, 2024

(54) MINIMALLY INVASIVE AUXILIARY TOOL FOR KNEE SURGERY

(71) Applicant: MEDACTA INTERNATIONAL SA, Castel San Pietro (CH)

(72) Inventors: Luka Cakic, Castel San Pietro (CH); Francesco Siccardi, Castel San Pietro (CH); Sascha Berberich, Castel San Pietro (CH); Riccardo Lucchini, Castel San Pietro (CH); Gianluca Parisi, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 687 days.

(21) Appl. No.: 17/274,644

(22) PCT Filed: Sep. 9, 2019

(86) PCT No.: PCT/IB2019/057564
§ 371 (c)(1),
(2) Date: Mar. 9, 2021

(87) PCT Pub. No.: WO2020/053731
PCT Pub. Date: Mar. 19, 2020

(65) Prior Publication Data
US 2021/0251642 A1    Aug. 19, 2021

(30) Foreign Application Priority Data
Sep. 10, 2018 (IT) .......................... 102018000008440

(51) Int. Cl.
*A61B 17/17* (2006.01)
(52) U.S. Cl.
CPC ...... *A61B 17/1764* (2013.01); *A61B 17/1714* (2013.01)

(58) Field of Classification Search
CPC ............... A61F 2/4684; A61B 17/1746; A61B 17/1764; A61B 17/1714
See application file for complete search history.

(56) References Cited

U.S. PATENT DOCUMENTS 6,022,356 A * 2/2000 Noyes ................ A61B 17/1764
606/88
6,086,592 A * 7/2000 Rosenberg ......... A61B 17/1714
606/86 R
(Continued)

FOREIGN PATENT DOCUMENTS

KR    101 525 165 B1    6/2015

OTHER PUBLICATIONS

International Search Report and Written Opinion for International Application No. PCT/IB2019/057564 dated Dec. 18, 2019, 10 pages.

*Primary Examiner* — Matthew J Lawson
(74) *Attorney, Agent, or Firm* — Meunier Carlin & Curfman LLC

(57) ABSTRACT

Various implementations described herein relate to a minimally invasive auxiliary tool for knee surgery. The tool comprises a handle in proximal position, a shaft defining an axis, and a shaped tip in distal position. In the tool: the handle, the shaft, and the shaped tip define a channel that connects the proximal end with the distal end of the tool; and the perimeter of the shaped tip comprises a plurality of sectors, wherein each sector is defined by a respective circular arc centred on the axis and wherein the circular arcs that define the various sectors have respective radii that are different the one from the others. Various implementations also include a kit comprising a tool and a bone reamer.

12 Claims, 3 Drawing Sheets

(56) References Cited

U.S. PATENT DOCUMENTS

| | | | | |
|---|---|---|---|---|
| 6,258,097 | B1* | 7/2001 | Cook | A61F 2/4657 |
| | | | | 606/91 |
| 7,572,258 | B2* | 8/2009 | Stiernborg | A61B 17/15 |
| | | | | 606/79 |
| 9,826,994 | B2* | 11/2017 | Eash | A61B 17/1778 |
| 2002/0099447 | A1* | 7/2002 | Mears | A61B 17/00234 |
| | | | | 623/22.4 |
| 2007/0123902 | A1* | 5/2007 | Berberich | A61B 17/1714 |
| | | | | 606/96 |
| 2010/0049200 | A1* | 2/2010 | Re | A61B 17/1714 |
| | | | | 606/86 R |
| 2012/0283709 | A1 | 11/2012 | Reichert et al. | |
| 2012/0323247 | A1* | 12/2012 | Bettenga | A61F 2/46 |
| | | | | 606/91 |
| 2022/0104835 | A1* | 4/2022 | Blaser | A61B 17/1668 |
| 2022/0117720 | A1* | 4/2022 | Ng | A61B 17/1764 |

\* cited by examiner

MINIMALLY INVASIVE AUXILIARY TOOL FOR KNEE SURGERY

The present invention relates to a minimally invasive tool intended to help a surgeon in the correct drilling of a bone, in particular in order to properly anchor the head of a ligament under reconstruction.

In the knee joint, the posterior cruciate ligament (PCL) plays a very important biomechanical role, particularly in providing the necessary stability to the joint.

As a result of major traumas, the ligament may suffer different degrees of injury. If the injury is partial, it is usually sufficient to use conservative procedures and to wait for the ligament to heal on its own. But if the injury is total, a ligament reconstruction operation is necessary to restore the correct functioning of the knee joint.

In this type of operation, a hole must first be created in the condyle of the femur to act as a housing for a head of the ligament under reconstruction. The position and diameter of the hole must be determined in such a way as to approximate as precisely as possible the insertion of the natural ligament. In so doing, the reconstructed ligament does not alter the biomechanics of the joint and restores its original functioning.

More specifically, the diameter and position of the ideal hole for inserting the reconstructed ligament need to approximate as precisely as possible the curvature of the patient's condyle.

The document U.S. Pat. No. 7,972,341 describes a tool intended to help a surgeon choose the size and position of the hole. This tool comprises a cannulated shaft equipped with a pistol handle at the proximal end and an interchangeable shaped tip at the distal end. A portion of the perimeter of the shaped tip is defined by a circular arc centred on the axis of the cannulated shaft. In the kit provided with the tool, various shaped tips are available and in each shaped tip the portion of the circular arc has a different radius. The use of the tool requires gradually bringing various shaped tips near to the condyle so as to be able to visually compare their respective radii and, thus, to identify the shaped tip that best approximates the natural curvature of the condyle. Once the most suitable shaped tip has been identified, it provides the measurement of the radius of the reamer head that must then be used to open the hole.

In addition, again by means of a visual comparison, the most appropriate shaped tip can easily be arranged so that the respective circular arc portion follows the curvature of the condyle. Once the shaped tip's correct position has been found, two small anchor tips that extend distally allow the instrument to be held firmly in place while a guidewire (typically a Kirschner wire) is inserted along the cannulated shaft. Thanks to the geometry of the tool, the guidewire is positioned in the centre of the circular arc that best approximates the curvature of the condyle. Once the guidewire has been inserted, the tool can be removed and the bone reamer with the most suitable reamer head, which had been identified previously, can be used to open the hole.

The applicant believes that this known tool, although widely used and appreciated, is not without room for improvement.

First of all, the system based on interchangeable shaped tips, although effective, is quite laborious and requires many successive operations in which the shaped tips are replaced before identifying the correct one. The different replacement operations of the shaped tips that follow one another result in a rather long overall time for arriving at the insertion of the guidewire.

In addition, the two anchor tips necessarily determine incisions in the cartilage of the joint. In cases where the cartilage is already damaged by trauma, the two small incisions do not result in a significant worsening of the overall condition of the knee. However, there are cases in which the cartilage is healthy despite the ligament being damaged. In these cases, the small incisions create additional damage that is added to the other, worsening the overall condition of the knee. Such damage is completely undesirable.

The purpose of the present invention is, therefore, to overcome the drawbacks highlighted above in relation to the prior art.

In particular, one of the tasks of the present invention is to provide an auxiliary tool for knee surgery that allows a simple and rapid procedure for choosing the size and positioning of the bone hole.

Another task of the present invention is to provide an auxiliary tool for knee surgery that does not result in cartilage injury when choosing the size and placement of the bone hole.

This purpose and these tasks are achieved by means of a tool in accordance with claim 1 and by means of a kit in accordance with claim 8. Additional advantages can be obtained by means of the optional technical features set out in the dependent claims.

In order to better understand the invention and to appreciate its advantages, some of its non-limiting embodiments are described below, referring to the attached drawings, wherein.

Figure 1:
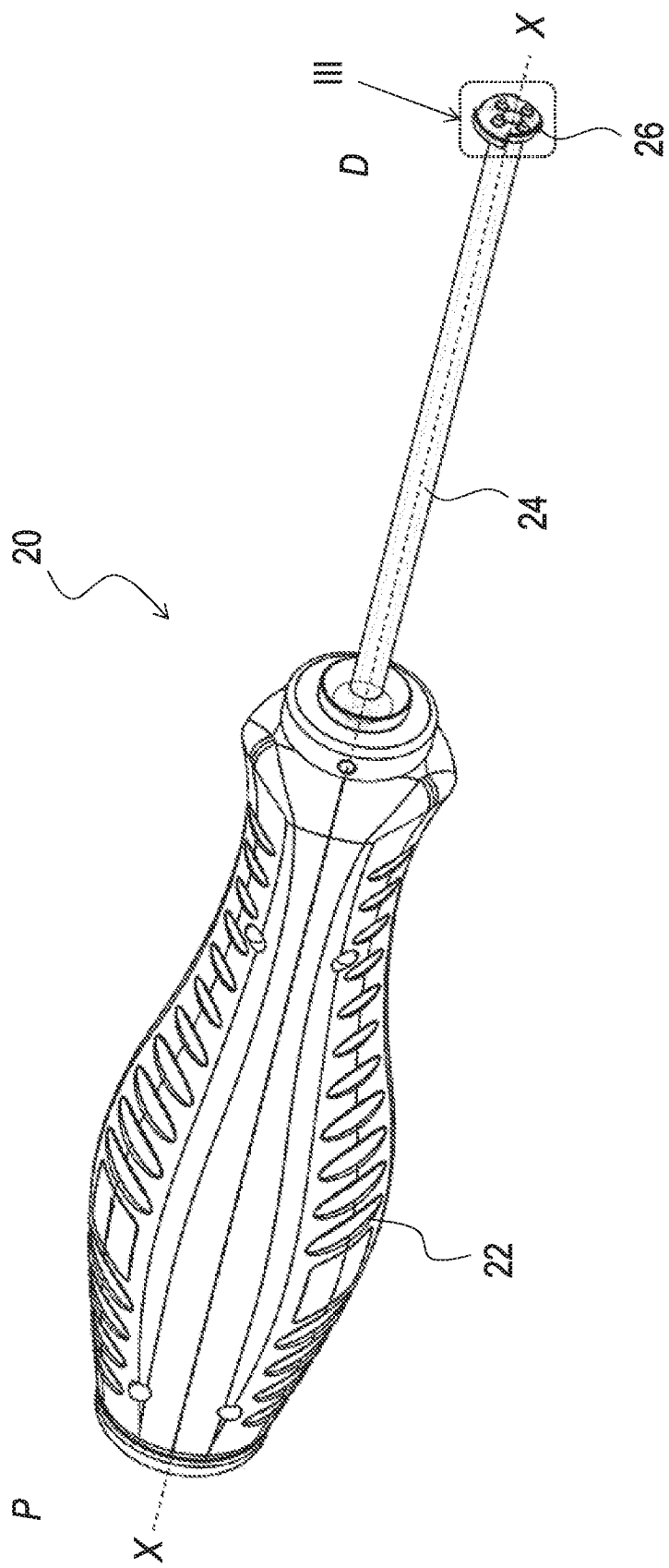
FIG. 1 shows a frontal-lateral perspective view of a tool according to the invention.
Figure 2:
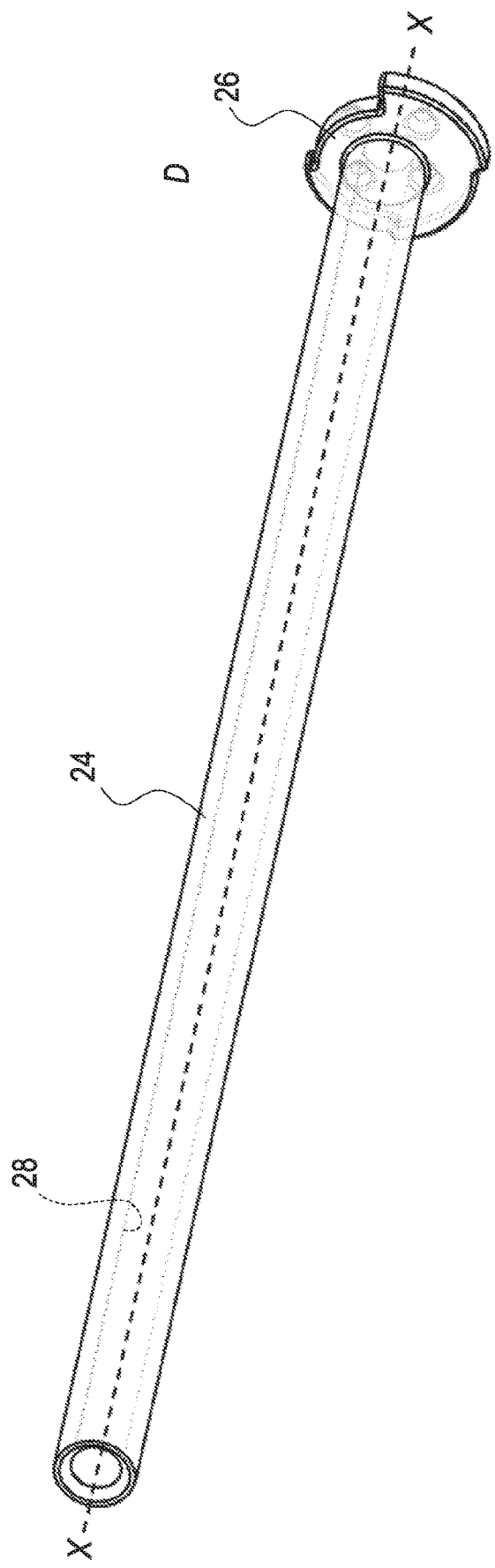
FIG. 2 shows a lateral-rear perspective view of a part of the tool in FIG. 1.

The invention relates to a minimally invasive auxiliary tool for knee surgery that is identified, as a whole, by the number 20. The tool 20 comprises a handle 22 in proximal position, a shaft 24 defining an axis X and a shaped tip 26 in a distal position, wherein the handle 22, the shaft 24, and the shaped tip 26 define a channel 28 that connects the proximal end P with the distal end D of the tool 20; and the perimeter of the shaped tip 26 comprises a plurality of sectors, wherein each sector 30 is defined by a respective circular arc 32 centred on the axis X and wherein the circular arcs 32 defining the various sectors 30 have different radii R from each other.

In the tool 20 according to the invention, the channel 28 preferably has a substantially straight development. Although slightly curved developments of the channel 28 can still guarantee the functionality of the tool 20, the straight development is what makes its use easier and more intuitive, and which limits its size as much as possible.

The handle 22 preferably develops mainly along the axis X, thus assuming the typical shape of the handle of the type used for screwdrivers (see FIG. 1). Although other shapes can be used for the handle 22, the shape shown in FIG. 1 is the one that limits the overall dimensions of the tool 20 in each use position. This feature will be further described below, with reference to the advantages that it implies in the use of the tool 20.

Above and below, the reference number 30 identifies either a single, a priori unspecified sector or the plurality of sectors as a whole. The reference numbers 301, 302 . . . 30n indicate, instead, the individual sectors when it is necessary to distinguish them from each other. A similar use is made with the reference numbers relating to other components that are present in the tool 20 in a plurality of examples, such as, for example, the circular arcs 32 and their respective radii R.

As already mentioned, the channel 28 connects the proximal end P with the distal end D of the tool 20. In other words, through the channel 28 it is possible to completely cross the tool 20 from side to side. For example, it is possible to insert a guidewire, typically a 2.4 mm diameter Kirschner wire, into the opening of the channel 28 at the proximal end P and push the guidewire along the channel 28 until it exits the opening at the distal end D.

In accordance with the embodiment represented in the attached figures, the shaped tip 26 comprises four sectors 301, 302, 303, and 304 that are defined, respectively, by the circular arcs 321, 322, 323, and 324 and that have, respectively, the radii $R_1$, $R_2$, $R_3$ and $R_4$. The following relation applies to this embodiment: $R_1<R_2<R_3<R_4$.

In accordance with other embodiments (not shown) the shaped tip 26 can comprise a different number of sectors 30.

The sectors 30 are preferably arranged in a progressive manner. In other words, it is preferable that, considering first the sector with the minimum radius:

Moving in a first direction, the other sectors are to be found arranged in ascending order of radius R; and Moving in the opposite direction, the sector with the maximum radius is to be found immediately adjacent.

Figure 4:
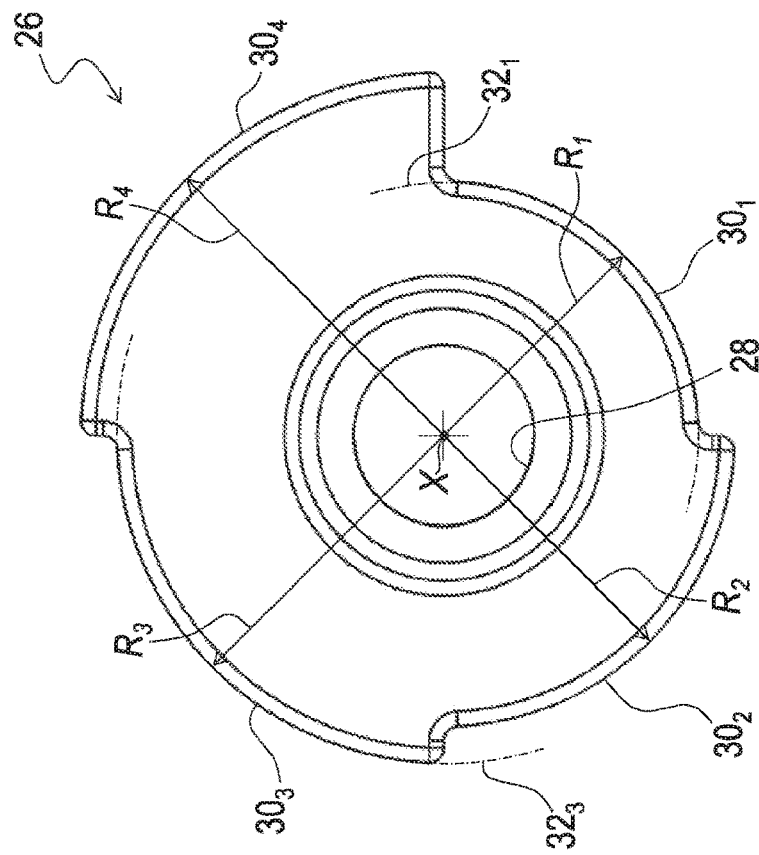
FIG. 4 shows an axial view of the detail in FIG. 3.

Therefore, with specific reference to the example in FIG. 4, starting from the sector 321 with the minimum radius $R_1$:

Moving clockwise, the other sectors 322, 323, and 324 are found arranged in ascending order of radius R; and Moving counter-clockwise, the sector 304 is found with the maximum radius of $R_4$.

The range of measurements within which the radii R are chosen can be defined on a statistical basis with reference to the condyle measurements in patients undergoing cruciate ligament reconstruction surgery. The radii R of the circular arcs 32 are, preferably, comprised between 2 mm and 6.5 mm, and, even more preferably, between 2.5 mm and 6 mm.

Similarly, the difference between two consecutive radii R can be defined on a statistical basis. The difference between two consecutive radii R is preferably between 0.2 mm and 0.8 mm, even more preferably between 0.4 mm and 0.6 mm.

Preferably, the shaped tip 26 further comprises a plurality of blunt studs 34 that extend in a distal direction along the axis X. The blunt studs 34 allow to obtain a firm support on the surface of the bone and of the cartilage for the tool 20. In addition, the fact that the studs are blunt prevents unwanted damage to the patient's cartilage.

Figure 3:
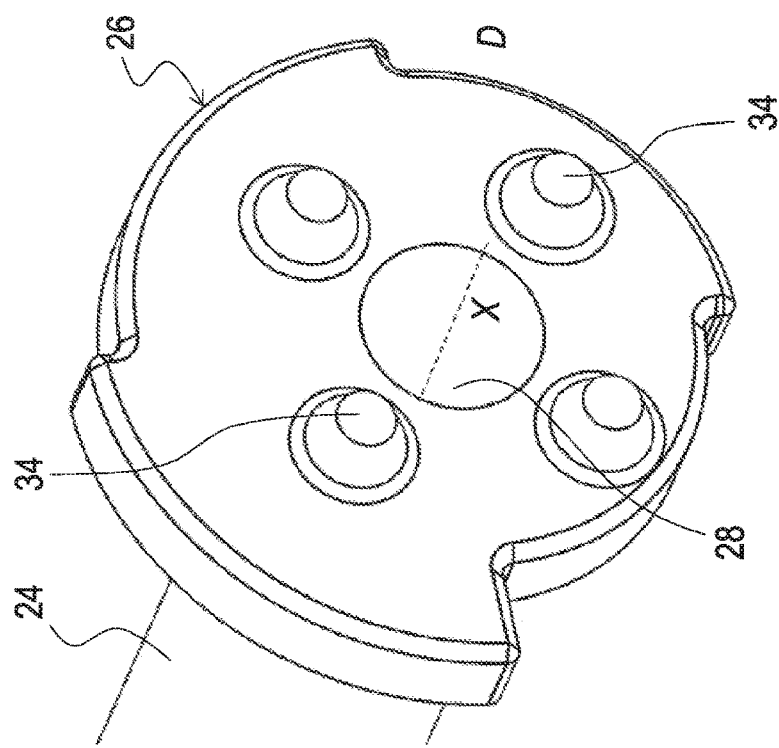
FIG. 3 shows an enlarged view of the detail identified as III in FIG. 1.

Preferably, the blunt studs 34 are four in number (see FIGS. 1 and 3), but in some embodiments they can be even fewer, for example three, or more.

Preferably, the tool 20 according to the invention is used in a kit that also comprises a bone reamer with a plurality of interchangeable reamer heads, wherein the various heads have different radii r from each other. Even more preferably, the radius r of each reamer head is equal to the radius R of a sector 30 of the shaped tip 26.

The following is a brief description of a method for using the tool 20 according to the invention during a posterior cruciate ligament reconstruction procedure.

The method essentially comprises the following steps:

making the cavity between the femur and the patient's tibia accessible at the rear;

accessing the cavity with the tool 20 by means of a translation mainly directed along the axis X;

placing the shaped tip 26 close to the patient's femur so that one sector 30 is in proximity of the condyle;

visually comparing the curvature of the condyle with that of the sector 30 closest to it;

rotating the tool 20 around the axis X until the optimal sector 30 is identified, the curvature of which best approximates that of the condyle;

taking note of the radius R of the optimal sector 30;

positioning the shaped tip 26 in such a way that the optimal sector 30 best approximates the curvature of the condyle;

placing the blunt studs 34 on the bone so that the tool 20 remains firmly in place;

inserting a guidewire along the channel 28;

implanting the guidewire firmly in the bone near the distal end D of the channel 28; and removing the tool 20 leaving the guidewire in place.

Preferably, the method further comprises the following steps:

selecting the optimal reamer head with a radius r equal to the radius R of the optimal sector 30;

mounting the optimal reamer head on the reamer;

inserting the reamer along the guidewire; and boring the femur from one side to the other.

As the skilled person may well understand in view of the method, the technical features described above in relation to the tool 20 result in some significant advantages.

For example, since the shaped tip 26 and the whole tool 20 are rotated around the axis X, the screwdriver shape shown in FIG. 1 for the handle 22 allows to maintain the minimum encumbrance in any angular position of the tool 20. A pistol-shaped handle might be more ergonomic in a single angular position of the tool 20, but rotating the tool around the axis X it will soon interfere with other encumbrances.

Furthermore, the progressive arrangement of the sectors 30 allows to minimise the movement of the shaped tip 26 and to make it extremely efficient in order to identify the optimal sector 30. In fact, thanks to this arrangement, one of the possible ways to identify the optimal sector 30 is to place a sector 30 with a lower radius R near the condyle and then to rotate the shaped tip 26 on the spot in a single direction until the optimal sector 30 is found.

Moreover, in the case of momentary indecision between two sectors 30 with similar radii, the progressive arrangement of the sectors 30 allows an extremely simple and rapid comparison to be made between the two sectors, since it is sufficient to rotate the shaped tip 26 a little. This limits errors in the choice of the reamer radius.

On the contrary, a non-progressive arrangement of the sectors 30 would require many more rotations of the shaped tip 26 in both directions and a greater risk of error in the choice.

As the skilled person can well understand, the invention enables to overcome the drawbacks highlighted above with reference to the prior art. In particular, the present invention provides an auxiliary tool for knee surgery that allows a simple and rapid procedure for the choice of the size and of the positioning of the bone hole. In fact, the comparison of the condyle with different sectors can be done simply by rotating the shaped tip 26 around the axis X, without any need to extract the tool and replace the shaped tip as required by the prior art.

In addition, the present invention provides an auxiliary tool for knee surgery that does not result in cartilage injury when choosing the size and placement of the bone hole. In fact, the blunt studs 34 that define the support on the bone do not cause any damage to the tissues.

It is clear that the specific features are described in relation to different embodiments of the invention with the intention of providing non-limiting examples. Obviously, a person skilled in the art can make further modifications and variations to the present invention, in order to satisfy contingent and specific needs. For example, the technical features described in relation to an embodiment of the invention may be extrapolated from it and applied to other embodiments of the invention. These modifications and variations are also included within the scope of protection of the invention, as defined by the following claims.

The invention claimed is:

1. A minimally invasive auxiliary tool for knee surgery, comprising: a handle in proximal position, a shaft defining an axis, and a shaped tip in distal position, wherein
   the handle, the shaft, and the shaped tip define a channel which connects a proximal end of the tool with a distal end of the tool, and
   a perimeter of the shaped tip comprises a plurality of sectors, wherein each sector is defined by a respective circular arc centered on the axis and wherein each sector has a respective radius that is different from the radii of the other sectors.

2. The tool according to claim 1, wherein the handle develops along the axis.

3. The tool according to claim 1, wherein the channel has a straight development.

4. The tool according to claim 1, wherein the radii of the circular arcs are between 2 mm and 6.5 mm.

5. The tool according to claim 4, wherein the radii of the circular arcs are between 2.5 mm and 6 mm.

6. The tool according to claim 1, wherein a difference between the radii of two circular arcs that are directly adjacent each other is between 0.2 mm and 0.8 mm.

7. The tool according to claim 6, wherein a difference between the radii of two circular arcs that are directly adjacent each other the difference is between 0.4 mm and 0.6 mm.

8. The tool according to claim 1, wherein the shaped tip comprises a plurality of blunt studs extending along the axis in distal direction.

9. The tool according to claim 1, wherein the sectors of the shaped tip are arranged in a progressive manner.

10. A kit comprising the tool according to claim 1 and a bone reamer comprising a plurality of interchangeable reamer heads, wherein each reamer head has a respective radius different from the other reamer heads.

11. The kit according to claim 10, wherein the radius of a respective reamer head of the plurality of interchangeable reamer heads is equal to the radius of a corresponding sector of the plurality of sectors of the shaped tip.

12. The tool according to claim 1, wherein each of the sectors are arranged circumferentially around the axis.

\* \* \* \* \*